US005571057A

United States Patent [19]

Ayers

[11] Patent Number: 5,571,057
[45] Date of Patent: Nov. 5, 1996

[54] APPARATUS AND METHOD FOR CHANGING A SEQUENCE OF VISUAL IMAGES

[76] Inventor: Margaret E. Ayers, 427 N. Canon Dr., Suite 209, Beverly Hills, Calif. 90210

[21] Appl. No.: 306,931

[22] Filed: Sep. 16, 1994

[51] Int. Cl.$^6$ ........................................ A63F 9/24
[52] U.S. Cl. ........................................ 463/36
[58] Field of Search ............... 128/782; 600/27, 600/26; 273/460, 433, 237, 85 G

[56] References Cited

U.S. PATENT DOCUMENTS

| | | | |
|---|---|---|---|
| 3,837,331 | 9/1974 | Ross | 128/732 X |
| 3,855,998 | 12/1974 | Hidalgo-Briceno | 128/732 |
| 3,875,930 | 4/1975 | Silva et al. | 128/732 |
| 4,149,716 | 4/1979 | Scudder . | |
| 4,461,301 | 7/1984 | Ochs | 128/630 |
| 4,632,126 | 12/1986 | Aguilar | 128/732 |
| 4,682,159 | 7/1987 | Davison | 340/709 |
| 4,800,893 | 1/1989 | Ross et al. | 128/732 |
| 4,919,143 | 4/1990 | Ayers | 128/732 |
| 4,949,726 | 8/1990 | Hartzell et al. | 273/460 X |
| 4,953,968 | 9/1990 | Sherwin et al. | 351/211 |
| 4,955,388 | 9/1990 | Silberstein | 128/731 |
| 5,001,632 | 3/1991 | Hall-Tipping | 364/413.04 |
| 5,024,235 | 6/1991 | Ayers | 128/732 |
| 5,092,835 | 3/1992 | Schurig et al. | 600/9 |
| 5,163,690 | 11/1992 | Davis et al. | 273/460 |
| 5,170,780 | 12/1992 | Rosenfeld | 128/731 |
| 5,213,338 | 5/1993 | Brotz | 273/460 |
| 5,343,871 | 9/1994 | Bittman et al. | 128/732 |

FOREIGN PATENT DOCUMENTS 0177075  9/1986  European Pat. Off. .......... A63F 9/22

*Primary Examiner*—Jessica J. Harrison
*Assistant Examiner*—Michael O'Neill
*Attorney, Agent, or Firm*—Cislo & Thomas

[57] ABSTRACT

A method and apparatus is provided for controlling video and film games by a player's (22) bioelectrical signals (44) comprising the steps of displaying a sequence of visual images having a predetermined control signal (62), obtaining an electroencephalographic (EEG) signal (44) from the player (22) while the player (22) is viewing the display of visual images, analyzing the EEG signal (44) to determine its magnitude, sending a signal (60) to the player (22) when the magnitude falls within a range of values corresponding to an amplitude threshold voltage (66) thereby causing the player (22) to mentally concentrate on the display (40) and affect a change on the magnitude of the EEG signal (44) which changes the sequence of visual images being displayed in accordance with the change in magnitude.

20 Claims, 2 Drawing Sheets

APPARATUS AND METHOD FOR CHANGING A SEQUENCE OF VISUAL IMAGES

BACKGROUND OF THE INVENTION

The present invention relates to video games and film games controlled by bioelectrical signals produced by a player's body, and more particularly, to the player changing and thereby controlling a sequence of visual images displayed by the video or film games by a corresponding change in the player's bioelectrical signals.

The introduction and rapid acceptance of video and film games over the past few years have to a great extent altered the traditional game market. Furthermore, video and film games are now being offered to the consumer as interactive games based on a digitized packet of information contained on such media as CD-Roms and the like.

Typically, the way these video and film games are played is that in order to participate in these types of games, the player inserts himself into the game's programming sequence by means of pre-arranged manual controls such as joy sticks and keyboards. By using the external devices, the player is able to participate in role events and fantasy or cartoon events.

Moreover, it is known that electroencephalograph (EEG) devices measure and record brain wave activity by sensing spontaneous electrical potential of a person's scalp, cerebrum or cortex at various sites. This spontaneous electrical potential measured by the EEG device is displayed as a frequency classified into four (4) basic frequency bands which are generally referred to as "delta", "theta", "alpha" and "beta"

Also, it is know in the art to use EEG signals in association with video and film games where a player interactively involves himself through the use of EEG devices. Typically, these types of games utilize the output from the EEG signals in association with visual displays wherein the player is able to produce various colored patterns, move objects in different directions or simulate exercise activity.

However, none of the prior art contemplates, discloses or claims an apparatus and method wherein a player is able in real time to change and thereby control a sequence of visual images through the use of a change in their EEG signals which conveys to the player a heightened sense of participation with the visual images displayed. The subject invention herein solves all of these problems in a new and unique manner which has not been part of the art previously. Some related patents are described below:

J. D. Scudder U.S. Pat. No. 4,149,716

This patent is directed to an apparatus for controlling a video game from signals generated from the firing of neuron impulses from a selected portion of the human body. Two or more sets of three electrodes are in physical and electrical contact with the human skin of one or more operators and are connected by wires to an electronic apparatus for amplifying, filtering, comparing and conditioning the neuron signals for controlling the display of the video game. The video display action on the video screen is controlled by the neuron signals in accordance with the internal game rules of a game chip that is electrically connected to the input signals.

G. R. Brotz U.S. Pat. No. 5,213,338

This patent is directed to a brain wave directed amusement device that operates on brain waves detected from one or more players and that produces a plurality of visual patterns and light arrangements. The device has an optical display pattern on its surface and receives a signal that is picked up from the players by electrodes attached to one player, and electrodes that are attached onto another player. The signals from these players are processed by a set of monitors and therein transmitted to the display device. The monitors can supply an audio signal to the players that is altered by the brain wave signal of the players.

D. W. Davis, et al. U.S. Pat. No. 5,163,690

This patent is directed to a game system that provides visual depiction of three-dimensional coordinate information derived from inputs of at least two players. The visual depiction allows players to modify their inputs to achieve game objectives. The game control inputs may utilize joysticks, slide switches, EEG alpha wave inputs, voice sound, or skin impedance signals. These signals are then scaled and combined to generate X, Y and Z coordinates.

G. R. Brotz U.S. Pat. No. 5,213,338

This patent is directed to an apparatus for controlling a cursor of a computer display. The apparatus includes a headset worn by a user and an ultrasonic transmitter which produces sound waves picked up by the headset which converts the sound waves into position change data used by a computer to control the cursor.

L. Ugo, et al. E.P. Pat. No. 177,075

This European patent is directed to a multi-functional device for using bioelectrical impulses picked up by electrodes incorporated in a headband worn by a player so that the frequency of the brain waves can be used to control a video game. Instead of existing manual controls, an electric signal is prearranged to pick up signals commanded by the brain that are amplified, filtered and modified to be compatible and to be inserted into the program of the electronic games.

SUMMARY OF THE INVENTION

The present invention is directed to an apparatus and method for controlling video and film games by utilizing a player's bioelectrical signals comprising the steps of displaying a sequence of visual images having a predetermined control signal, obtaining an electroencephalographic (EEG) signal from the player while the player is viewing the display of visual images, analyzing the EEG signal to determine its magnitude, and sending a signal to the player when the magnitude falls within a range of values corresponding to an amplitude threshold voltage thereby causing the player to mentally concentrate on the display and affect a change on the magnitude of the EEG signal which changes the sequence of visual images being displayed in accordance with the change in magnitude.

In use, the method of detecting analog bioelectrical frequencies in a player's body comprises the steps of detecting an analog bioelectrical signal at a selected location in the player's body, amplifying the analog bioelectrical signal, converting the analog bioelectrical signal to digital signals representing particular frequencies and selecting a particular digital signal of interest for use in changing the sequence of visual images that are currently being viewed by the player.

The apparatus used to perform the above method comprises a receptor means for attachment to a selected location of the player's body for receiving the analog bioelectrical signal, an amplifier for amplifying the analog bioelectrical signal received by the receptor means and associated therewith, and an analog to digital converter for converting the analog bioelectrical signal to digital signals representing a set of corresponding frequencies.

Accordingly, it is an object of the present invention to enable the manipulation of a sequence of visual images by utilizing bioelectrical signals, rather than utilizing manual control of electric or mechanical devices to control the sequence of visual displays in video and film display games.

It is a further object of the present invention to enable a player in real time to change a sequence of visual images through the use of a change in their EEG signals which conveys to the player a heightened sense of participation with the visual images displayed.

Other aspects and advantages of the present invention will become apparent from the following description of the preferred embodiments, taken in conjunction with the accompanying drawings, which illustrate, by way of example, the principles of the present invention.

BRIEF DESCRIPTION OF THE DRAWINGS

The above, as well as other, advantages of the present invention will become readily apparent to those skilled in the art from the following detailed description of the preferred embodiments when considered in the light of the accompanying drawings in which.

DESCRIPTION OF THE PREFERRED EMBODIMENTS

Figure 1:
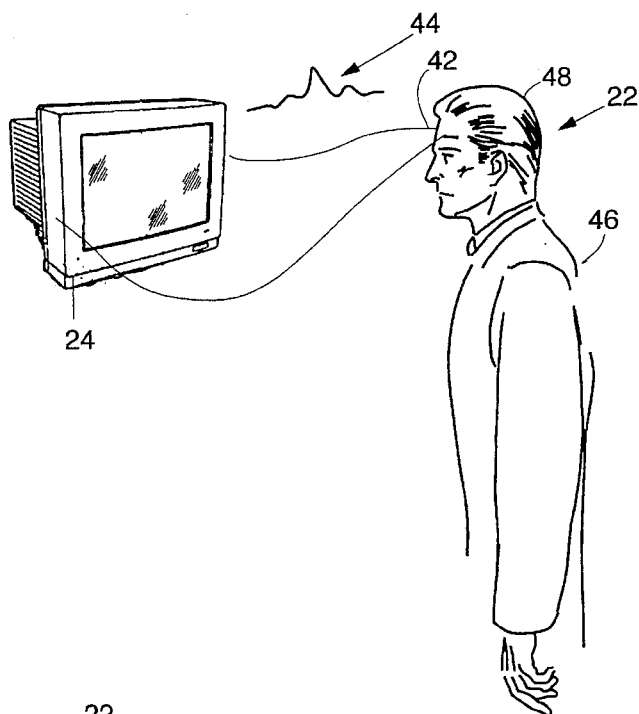
FIG. 1 is an illustration of a method for receiving bioelectrical signals from a player.

Referring now to the drawings wherein like reference numerals refer to like and corresponding part throughout, the apparatus for changing a sequence of visual images is generally indicated by numeral 20. Referring now to FIG. 1, a player's 22 bioelectrical signals 44 are measured through the use of a receptor means 24. The receptor means 24 comprises at least two electrodes 42 of a ferrous materials shown attached to the player 22. The electrodes 42 can be placed on any portion of the player's body 46 where bioelectrical signals 44 may be of interest. As shown in FIG. 1, in the preferred embodiment the bioelectrical signals 44 are measured from the head 48 of the player 22.

Figure 2:
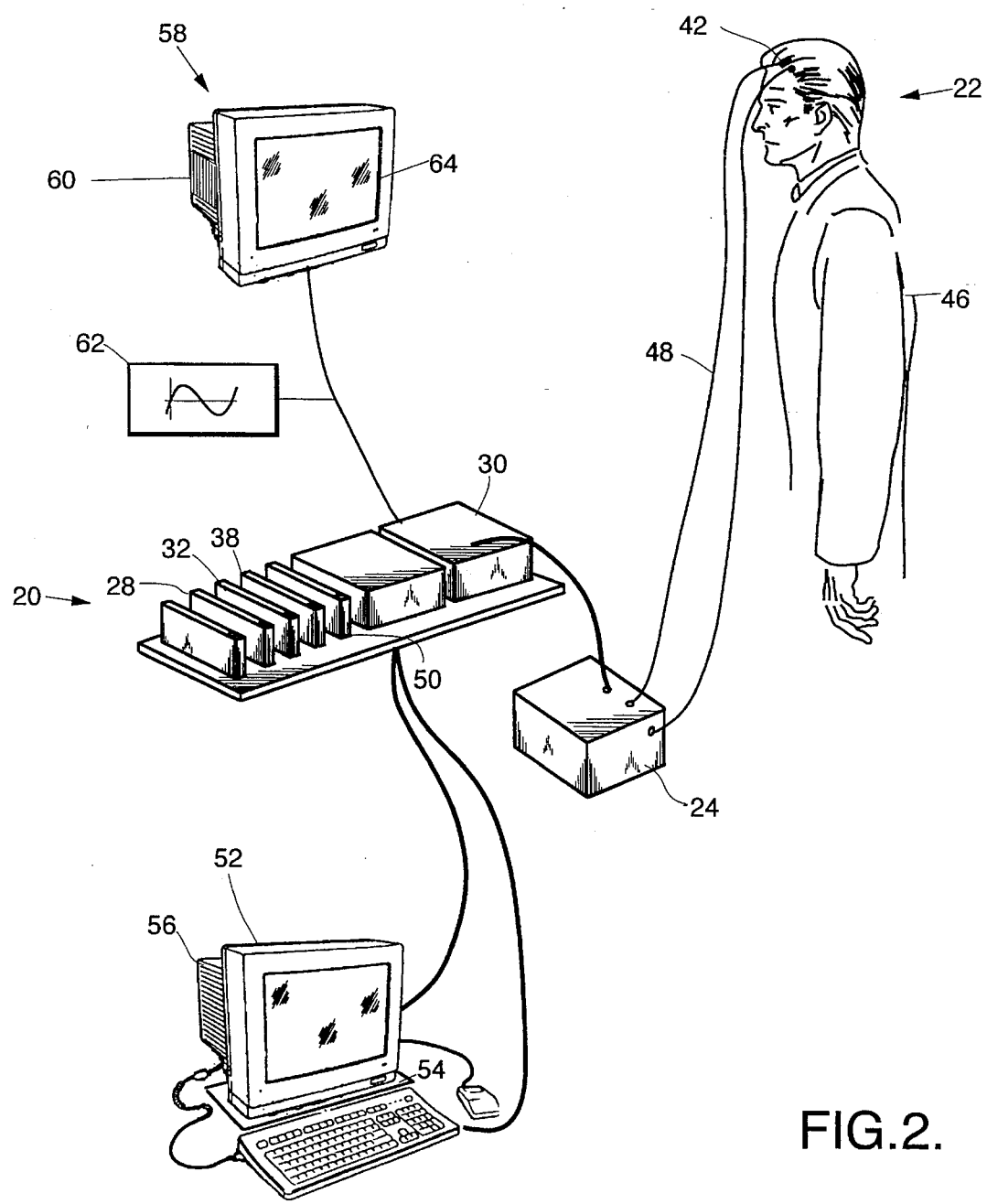
FIG. 2 is an illustration of a system for carrying out the invention.

An illustration of a system for practicing this invention is shown in FIG. 2 and comprises measuring a player's bioelectrical or electroencephalographic (EEG) signals 44 by the aforementioned receptor means 24 while the player 22 views a sequence of visual images having a predetermined control signal 62. In the preferred embodiment the sequence of visual images is displayed on a television monitor or set 64 or a device which displays holograms or may be any type of apparatus for displaying visual images known in the art.

The predetermined control signal 62 is superimposed onto the television monitor or set 64 displaying an initial sequence of visual images and comprises a light signal or flicker the intensity of which varies at a predetermined sinusoidal frequency. In the preferred embodiment the predetermined sinusoidal frequency is in the range of 1 Hz to 500 Hz which corresponds to the known measured frequency of EEG signals. In an alternative embodiment the predetermined control signal 62 may comprise a sinusoidal variation of the brightness of the sequence of visual images as they are being displayed.

Figure 3:
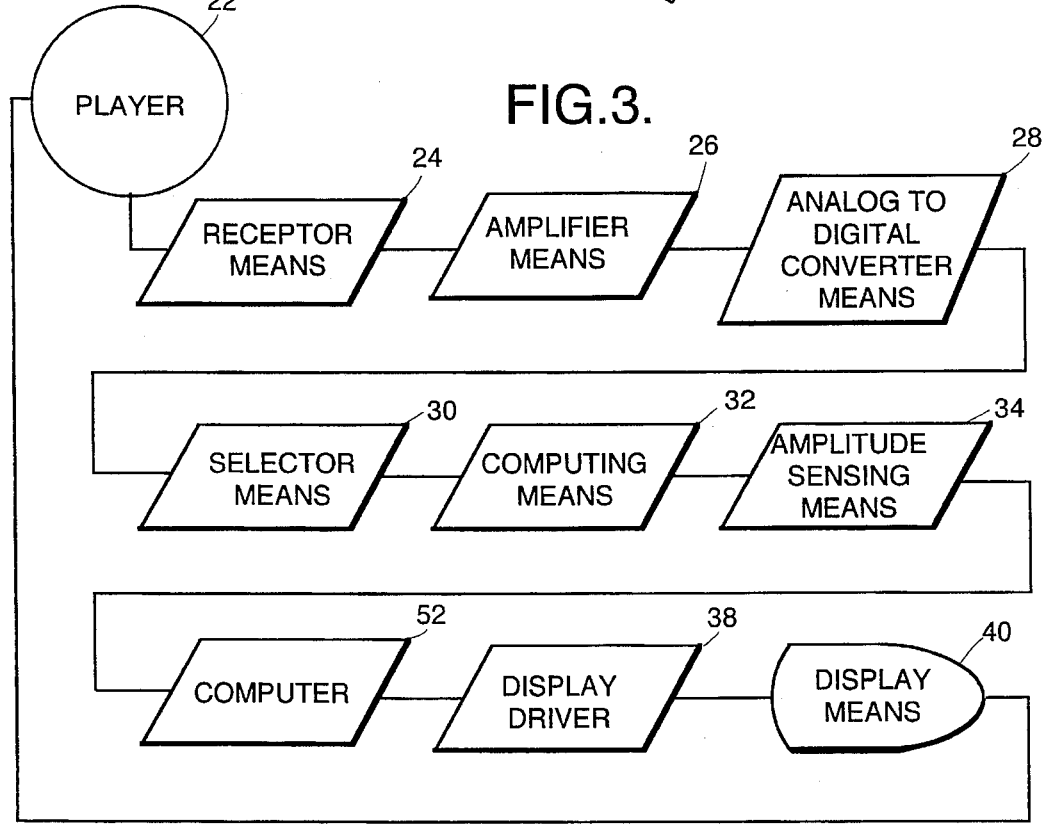
FIG. 3 is a system block diagram in accordance with an embodiment of this invention.

A block diagram of a system for practicing this invention is shown in FIG. 3 wherein the voltage potentials between the two electrodes 42 that are sensed by receptor means 24 when the player is viewing the initial sequence of images including control signal 62 is transmitted by wires, lazer beams or radio waves 48 to an amplifying means or high gain amplifier 26, as shown in FIG. 2. In the preferred embodiment, the high gain amplifier used is the morendocino microcomputer EEG amplifier or its equivalent. The high gain amplifier 26 is of a kind that can amplify very small analog signals such as the bioelectrical signals 44 produced in human beings. Such amplifiers 26 are commonly known in the art of electroencephelgraphic applications such as Grass P511-K amplifiers which can amplify bioelectrical signals 375,000 times in signal strength.

Once the analog bioelectrical signal 44 is sufficiently amplified, the signal 44 can be digitized or demodulated by an analog to digital converter means 28 so as to produce discrete digital signals which correspond to the analog frequencies inherent in the analog bioelectric signal 44. Additionally, it may be necessary that the outputs from the high gain amplifier 26 be coupled to band pass filters having a pass band in the range of 1 to 500 Hz to properly process the analog bioelectric signal 44 prior to demodulation.

In the preferred embodiment, the digitization or demodulation of the analog bioelectric signal 44 can be achieved by using a DASH-16 analog/digital input card 50. The input card 50 is manufactured by Metrabyted Corp., and is a high speed multifunction analog/digital I/O expansion board for use with a personal computer. The DASH-16 analog/digital input card 50 uses an industry standard (HI-674A) 12 bit successive approximation converter having a 12 microsecond conversion time. The input card 50 is switch selectable providing a choice between 16 single ended channels or 8 differential channels with 90 dB common mode rejection and +/−10 v common mode range.

The input impedance ranges common to all channels for the input card 50 are as follows: +1 v, +2 v, +5 v & +10 v unipolar and +/−0.5 v, +/−1 v, +/−2.5 v, +/−5 v +/−10 v bipolar and are controlled by the gain of an input instrumentation amplifier. Alternatively, these ranges may be changed with a single user installed resistor. All inputs are multiplexed through a low drift, fast settling instrumentation amplifier/sample-hold combination wherein once again the channel input configuration is switch selectable to operate as either 16 single ended or 8 differential channels.

The DASH-16 analog/digital input card 50 utilizes a 3 channel programmable interval timer which provides the necessary trigger pulses for the input card 50 at any rate from 250 KHz to 1 pulse/hr. Two of the channels of the programmable interval timer are dedicated to be operated in a fixed divider configuration from an internal 1 MHz crystal clock. The third channel is uncommitted and provides a gated 16 bit binary counter that can be used for event or pulse counting, delayed triggering, and in conjunction with the other channels for frequency and period measurement. In the preferred embodiment the 3 channel programmable interval timer is an Intel 8254 chip or equivalent.

In the preferred embodiment the D/A converters may be operated with a fixed −5 v reference available from the DASH-16 analog/digital input card 50 to give a −5 v (+/−0.05 v) precision reference voltage output. Alternatively, an external D.C. or A.C. reference may be used to give different output ranges. Typically the DASH-16 analog/digital input card 50 is double-buffered to provide instantaneous single step update. The digital input/output from the input card 50 comprises of 4 bits of TTL/DTL or CMOS compatible digital output and 4 bits of digital input.

As shown in FIG. 2, the analog/digital input card 50 is incorporated within a modified personal computer 52 which can be of an IBM PC or XT type sufficient to interface with the DASH-16 analog/digital input card 50. The numbers, parameters and commercial brand names just given are exemplary and not absolute and may be substituted by analog-to-digital converters known in the art of signal processing.

Next, the digital signals resulting from the DASH-16 analog/digital input card 50 are further analyzed to determine if certain analog bioelectric frequencies 44 are being generated by the player 22. A selector means 30 allows sufficient manipulation of the digital signals so as to separate particular digital signals which correspond to the particular bioelectric analog frequencies to be used in changing the sequence of visual images. This function can also be achieved by using the DASH-16 analog/digital input card 50.

The computer 52 selects from the digital signals the particular digital signal that corresponds to the analog frequency of the predetermined control signal 62. Such a selection can be performed by digital separation using certain digital filters commonly known in the art of digital filtering. In use the computer 52 performs the selection of the digital signal by use of an 8087 numerical processor card 54 with an expanded memory card 60. Alternatively, the selection technique can be implemented by use of the DASH-16 analog/digital input card 50.

A computing means 32 is used to integrate the amplitude of the particular digital signal over a pre-determined time duration. The resulting value is divided by microvoltage to determine a change in voltage with respect to time duration, and thereby determine that the bioelectric frequency emitted by the player 22 corresponds to the frequency of the predetermined control signal 62. This calculation is achieved by the computer 52 driven by particular algorithms such as Fourier analysis techniques.

The resulting voltage value from computing means 32 is compared to an established threshold amplitude voltage by an amplitude sensing means 35 and when the amplitude of the resulting signal is within a certain amplitude range (the bioelectric signal is within the particular frequency of control signal 62) a signaling means signals to the player 22 an auditory, visual or tactile movement signal indicating that the bioelectric frequencies being generated by the player 22 are now within the pre-determined range to change the sequence of visual images being displayed and the control signal 62 is turned off. The amplitude sensing means 5 may be a simple algorithm preset programmed within computer 52.

The signaling means 58 may simply be a light box or sound box 60 that emits a sound or light or series of sounds or lights which indicate to the player 22 that the bioelectric signals 44 received by the monitoring electrodes 42 are within a preset frequency range. Of course, the signaling means 58 can also be any other type of stimuli that can be sensed by the player 22 by displaying animations on the display means 40.

Once the player 22 is aware that his bioelectrical signals 44 are within a certain range which can be sensed, a feedback phenomenon is possible. The player 22 mentally concentrates on the sequence of visual images shown by the display means 40 upon obtaining the stimuli from the signaling means 58 and thereby, alter the bioelectrical signals 44 produced at the location of the electrodes 42. Bioelectric frequencies of a predetermined kind can either be facilitated and produced more readily or inhibited once the player 22 can be alerted to whether those frequencies produced are within the preset range.

Furthermore, a suppression means 68 can be used to suppress unwanted signals that would normally trigger the signaling means 68. These unwanted signals include "noise" attributable to the resulting bioelectric activity generated by the player's 22 muscular activity. The structure and function of the suppression means 68 are commonly known in the art and are not further herein discussed. Suffice it to say that extraneous bioelectric frequencies not of interest emanating from a location not around the electrodes 42 can be suppressed.

The actual data utilized by the computer 52 to change the sequence of visual images are the values of the real time microvoltage representing the particular frequencies of interest making up the bioelectric signal 44 in relationship to the frequency over time. Upper and lower threshold voltage levels are stored within computer 52 which correlate to particular bioelectric frequencies. When the amplitude of the sinusoidal wave measured by the electrodes 42 exceeds either the upper or lower threshold voltage limits, the computer 52 sends a signal to a display driver 38 to change the sequence of visual images shown by display means 40. The output from the display 38 may be in either digital or analog format by use of any conventional A/D converters known in the signal processing arts.

This process is repeated with a new set of upper and lower threshold voltage levels chosen by the computer 52 depending upon the prior change in the amplitude of the bioelectrical signal 44 being measured by electrodes 42. When the measured bioelectrical signal is within the threshold voltage range being compared by computer 52, the sequence of visual images remains the same.

The display driver 38 comprises a wide variety of different sequences of visual images and is a matter of design choice. By way of example, but not of limitation, the sequences of visual images may convey to the player 22 upon producing the correct frequency the ability to fly through various parts of a country, or experience various types of other pleasing environments.

A timing means 70 comprising timing circuitry commonly known in the art can be used to time the required duration that the level of bioelectric frequency production must stay within proscribed limits before a change in the sequence of visual images is to occur. The duration can be lessened once the player 22 has improved his ability to inhibit the production of certain bioelectric frequencies. Variability of the duration is a feature which conveys to the player 22 a heightened sense of participation with the visual images being displayed and additionally indicates a level of skill that has been developed by the player 22.

It should be indicated also, that a number of different EEG type channels can be fed into the invention for purposes of monitoring various areas provided the proper software and hardware modifications are adapted as known in the art of EEG monitoring and recording. A large number of cables, plugs, and jacks necessary for proper operation of the invention are not herein described as those accessory items are commonly known in the art of data processing with a microcomputer.

There has been described and illustrated herein an improved apparatus and method for changing a sequence of visual images. While particular embodiments of the invention have been described, it is not intended that the invention be limited exactly thereto, as it is intended that the invention be as broad in scope as the art will permit. The foregoing description and drawings will suggest other embodiments and variations within the scope of the claims to those skilled in the art, all of which are intended to be included in the spirit of the invention as herein set forth.

What is claimed is:

1. An improved method of changing a sequence of visual images, by means of application of a measured player's bioelectrical signals in combination with said sequence of visual images, said method comprising the steps of:

(a) displaying a sequence of visual images including a control signal having a preselected frequency;

(b) detecting an analog bioelectrical signal at a selected location of a player's body while said sequence of visual images are being viewed;

(c) amplifying said analog bioelectrical signal;

(d) converting said analog bioelectrical signal to digital signals representing particular frequencies;

(e) selecting a particular digital signal which corresponds in frequency to said control signal;

(f) establishing an amplitude threshold voltage without delay and distortion resulting from bandpass and spectral analysis for said particular digital signal;

(g) wherein said method further comprises the steps of sending a signal to said player when said particular digital signal falls within said amplitude threshold for a predetermined duration; and (h) causing said player to mentally concentrate so as to affect a change of amplitude of said digital signal thereby displaying a next sequence of visual images in accordance with said change.

2. An improved method as claimed in claim 1, wherein said step of displaying a sequence of visual images is achieved by using a television monitor.

3. An improved method as claimed in claim 1, wherein said step of detecting an analog bioelectrical signal is achieved by using at least two electrodes positioned at said selected location of said player's body for measuring a voltage potential.

4. An improved method as claimed in claim 3, wherein said step of amplifying is achieved by using a signal amplifier associated with said electrodes and which recognizes said voltage potential between said electrodes.

5. An improved method as claimed in claim 4, wherein said step of converting is achieved by receiving signals from said signal amplifier representing voltage variations over time and using a means for converting said voltage variations to convert said voltage variations into digital pulses.

6. An improved method as claimed in claim 5, wherein said step of selecting is achieved using a means for analyzing said digital pulses which receives said digital pulses corresponding to particular analog bioelectrical frequencies.

7. An improved method as claimed in claim 1 wherein subsequent to said step of establishing an amplitude for said particular digital signal, an additional step includes, integrating the amplitude of said selected digital signal with respect to duration and dividing a resulting value by said amplitude threshold voltage yielding a determination of whether voltage of said selected digital signal is changing, and thereby whether said next sequence of visual images is to be displayed.

8. An improved method as claimed in claim 6, wherein said step of sending is achieved by use of a means for displaying a sensation to said player when said analog bioelectrical frequency recognized between said electrodes falls within a predetermined range for a predetermined duration.

9. An improved method as claimed in claim 1, wherein said preselected frequency is in the range 1 to 500 Hz.

10. An improved method as claimed in claim 1, further comprising the step of suppressing extraneous signals unrelated to said analog bioelectrical signal.

11. An improved apparatus for changing a sequence of visual images, by means of application of a measured player's bioelectrical signals comprising:

(a) display means for displaying a sequence of visual images including a control signal means having a preselected analog frequency;

(b) receptor means for attachment to a player's body at a location emitting an analog bioelectrical signal whilst said sequence of visual images are being viewed;

(c) amplification means for amplifying said analog bioelectrical signal received from said receptor means, said receptor means conveying said analog bioelectrical signal to said amplification means;

(d) analog to digital converter means for converting said analog bioelectrical signal to digital signals representing particular analog frequencies, said analog signal having been amplified is converted to discrete digital signals representing corresponding analog frequencies;

(e) selecting means to select a particular digital signal, said selecting means including a numerical analyzer receiving said discrete digital signals allowing the selection of a particular digital signal which corresponds in analog frequency to said control signal means to be inhibited or accentuated and avoiding the delay and distortion of power spectral and bandpass analysis; and (f) signaling means for giving said player a particular sensation when said particular digital signal is maintained within predetermined ranges of amplitude for a predetermined duration, thereby allowing said player to mentally concentrate so as to effect a change of amplitude of said particular digital signal thereby displaying a next sequence of visual images in accordance with said change when said player receives said sensation.

12. An improved apparatus as claimed in claim 11, wherein said displaying means for displaying a sequence of visual images is achieved by using a television monitor.

13. An improved apparatus as claimed in claim 11, wherein said receptor means comprises at least two electrodes associated with said amplification means for measuring a voltage potential positioned at said location emitting said analog bioelectrical signal in said player's body.

14. An improved apparatus as claimed in claim 13, wherein said amplification means comprises using a signal amplifier associated with said electrodes and which recognizes said voltage potential between said electrodes.

15. An improved apparatus as claimed in claim 14, wherein said analog-to-digital converter means comprises receiving signals from said signal amplifier representing voltage variations over time and using a means for converting said voltage variations to convert said voltage variations into digital pulses.

16. An improved apparatus as claimed in claim 11, further comprising an integrating means for establishing said predetermined amplitude ranges for a predetermined duration, wherein said mens integrates the amplitude of said particular digital signal with respect to duration and divides a resulting value by a predetermined amplitude threshold voltage, thereby allowing the determination of whether voltage of said selected digital signal is changing, and thereby whether said next sequence of visual images is to be displayed.

17. An improved apparatus as claimed in claim 15, wherein said signaling means comprises a means for displaying a sensation to said player when said analog bioelectrical frequency recognized between said electrodes falls within a predetermined range for a predetermined duration.

18. An improved apparatus as claimed in claim 11, wherein said displaying means for displaying a sequence of visual images is achieved by using holograms.

19. An improved apparatus as claimed in claim 11, further comprising a suppression means for suppressing unwanted signals received by said receptor means which can be selectively set to prevent said unwanted signals received by said receptor means.

20. An improved method of changing a sequence of visual images, by means of application of a measured player's bioelectrical signals in combination with said sequence of visual images, said method comprising the steps of:

(a) a displaying a sequence of visual images including a control signal having a preselected frequency;

(b) detecting an analog bioelectrical signal at a selected location of a player's body using at least two electrodes positioned at said selected location of said player's body for measuring a voltage potential while said sequence of visual images are being viewed;

(c) suppressing extraneous signals unrelated to said analog bioelectrical signal;

(d) amplifying said analog bioelectrical signal by using a signal amplifier associated with said electrodes and which recognizes said voltage potential between said electrodes;

(e) converting said analog bioelectrical signal to digital signals representing particular frequencies by receiving signals from said signal amplifier representing voltage variations over time and using a means for converting said voltage variations to convert said voltage variations into digital pulses;

(f) selecting a particular digital signal which corresponds in frequency to said control signal using a means for analyzing said digital pulses which receives said digital pulses corresponding to particular analog bioelectrical frequencies;

(g) establishing an amplitude threshold voltage without delay and distortion resulting from bandpass and spectral analysis for said particular digital signal;

(h) wherein said method further comprises the steps of sending a signal to said player when said particular digital signal falls within said amplitude threshold for a predetermined duration; and (i) causing said player to mentally concentrate so as to affect a change of amplitude of said digital signal thereby displaying a next sequence of visual images in accordance with said change.

* * * * *